United States Patent
Konya et al.

(10) Patent No.: US 9,877,676 B2
(45) Date of Patent: Jan. 30, 2018

(54) OPTIMIZED LANCET TAPE

(75) Inventors: Ahmet Konya, Ludwigshafen (DE); Bernd Hiller, Lampertheim (DE)

(73) Assignee: Roche Diabetes Care, Inc., Indianapolis, IN (US)

(*) Notice: Subject to any disclaimer, the term of this patent is extended or adjusted under 35 U.S.C. 154(b) by 0 days.

(21) Appl. No.: 13/348,880

(22) Filed: Jan. 12, 2012

(65) Prior Publication Data

US 2012/0184875 A1 Jul. 19, 2012

Related U.S. Application Data

(63) Continuation of application No. PCT/EP2010/060109, filed on Jul. 14, 2010.

(30) Foreign Application Priority Data

Jul. 14, 2009 (EP) ..................................... 09165424

(51) Int. Cl.
*A61B 5/151* (2006.01)
*A61B 5/15* (2006.01)

(52) U.S. Cl.
CPC .... *A61B 5/15146* (2013.01); *A61B 5/150022* (2013.01); *A61B 5/15153* (2013.01); *A61B 5/15169* (2013.01); *A61B 5/15171* (2013.01); *A61B 5/150282* (2013.01); *A61B 5/150435* (2013.01); *A61B 5/150503* (2013.01); *Y10T 156/10* (2015.01); *Y10T 156/1051* (2015.01); *Y10T 156/1702* (2015.01)

(58) Field of Classification Search
CPC ............ A61B 5/15171; A61B 5/15169; A61B 5/15148; A61B 5/15146; B65B 9/06; B65B 9/067; B65B 9/073; B65B 2220/22; B65B 9/0206

USPC .................................. 600/584; 606/181–183
See application file for complete search history.

(56) References Cited

U.S. PATENT DOCUMENTS

| | | | | |
|---|---|---|---|---|
| 3,665,672 A | * | 5/1972 | Speelman | ........................ 53/435 |
| 2005/0227410 A1 | * | 10/2005 | Colella et al. | ................ 438/106 |
| 2005/0245845 A1 | * | 11/2005 | Roe et al. | ..................... 600/583 |
| 2007/0173740 A1 | * | 7/2007 | Chan et al. | ................... 600/583 |
| 2009/0010802 A1 | | 1/2009 | Joseph et al. | |
| 2010/0145376 A1 | | 6/2010 | Konya et al. | |
| 2010/0216246 A1 | | 8/2010 | Konya et al. | |
| 2010/0292609 A1 | | 11/2010 | Zimmer et al. | |

FOREIGN PATENT DOCUMENTS

| | | |
|---|---|---|
| DE | 2803345 B1 | 6/1979 |
| EP | 1360935 A1 | 11/2003 |
| EP | 1990001 A1 * | 5/2007 |
| EP | 1992284 A1 * | 5/2007 |
| WO | 2007077212 A2 | 7/2007 |
| WO | 2007147494 A2 | 12/2007 |
| WO | 2008043565 A2 | 4/2008 |
| WO | 2009036986 A2 | 3/2009 |

* cited by examiner

*Primary Examiner* — Sean Dougherty
(74) *Attorney, Agent, or Firm* — Harness, Dickey & Pierce, P.L.C.

(57) ABSTRACT

A method for producing an analytical tape, in particular a lancet tape, is proposed. The analytical tape is designed for being used in an analytical testing device with at least a sample-taking function. In the method, at least one supporting tape is provided in a continuous process. A plurality of lancet elements are successively applied directly to the supporting tape at at least one application point.

38 Claims, 5 Drawing Sheets

OPTIMIZED LANCET TAPE

CROSS-REFERENCE TO RELATED APPLICATIONS

This application is a continuation of International Application No. PCT/EP2010/060109, filed on Jul. 14, 2010, which claims the benefit and priority of European Patent Application No. 09165424.4, filed Jul. 14, 2009. The entire disclosures of the above applications are incorporated herein by reference.

BACKGROUND

The invention relates to a method for producing an analytical tape, in particular a lancet tape. The invention also relates to an analytical tape and an analytical testing device which comprises such an analytical tape. Furthermore, an apparatus for producing an analytical tape is proposed. Such methods, analytical tapes, analytical testing devices and apparatuses are used in particular in medical diagnostics, for example by private individuals, in the care sector or in the hospital sector, in order to monitor a concentration of one or more analytes in a body fluid of a user, for example for monitoring a blood glucose concentration. Alternatively or in addition, other applications are also possible.

Various test methods are known for monitoring an analytical concentration in a body fluid of a user, for example a patient or a person susceptible to certain illnesses. For instance, there are known test methods in which, for example, the user must produce a specimen of the body fluid and investigate it for its analyte concentration seven times a day. In order that this need to investigate his or her body fluid, for example blood, does not impinge more than necessary on the users's daily routine, analytical testing devices which are easy and quick to handle and, for example, are configured as handheld devices have been developed.

In the meantime, there are known analytical testing devices which operate with one or more analytical tapes, to which a number of analytical aids have been applied and can be successively used. These analytical aids may comprise, for example, test pads by means of which a specimen of the body fluid can be investigated. Alternatively or in addition, the analytical aids may also comprise lancet elements, by means of which a prick or incision can be made in the user's skin in order in this way to produce a specimen of the body fluid. The present invention refers in particular to analytical tapes with a number of lancet elements, and to the production thereof.

One particular difficulty with such analytical tapes with lancet elements, which are also referred to hereafter as lancet tapes, is that of achieving defect-free and sterile production of these test tapes. The analytical testing devices generally have a transporting mechanism, for example a transporting mechanism with a gripper, by means of which a lancet element can be respectively positioned in a position for use. In order not to disturb the operating sequence of the analytical testing devices, the analytical tapes have to meet demanding requirements in terms of precision.

WO 2007/147494 A2 describes a system which comprises disposable medical elements and a packaging tape. The packaging tape comprises a plurality of chambers in which the disposable medical elements are accommodated. The tape is accommodated in the system in a folded state.

WO 2008/043565 A2 describes a sampling system with lancets, in which a protective cover is automatically removed from a lancet and a test pad is unpacked before said lancet is used. In this case, connecting adhesive tapes are used to apply the lancets to a supporting tape.

EP 1992284 A1 (see also US 2010/0292609 A1) discloses a method for magazining pricking elements and a tape magazine. In this case, a multiplicity of disposable lancets provided with a lancet tip for pricking the skin are provided wound up on a roller, or a supporting tape that can be wound up, for obtaining a specimen of body fluid. The lancets are respectively arranged in a package, the lancet packages formed in this way being individually applied to the supporting tape and fixed thereupon.

In the case of known test tapes, however, there is a technical challenge insofar as these test tapes can in practice present transporting difficulties in analytical testing devices that operate on an indexing principle, such as for example the analytical system described in WO 2008/138443 A1 (see also US 2010/0145376 A1). For instance, an indexing mechanism generally has a height-sensitive element which responds to the thickness of the analytical tape. This device is used for positioning the elements, for example the lancets. However, this mechanical sensor reacts when there is any change in thickness of the analytical tape. Consequently, in the case of the tapes known from the prior art, this may also take place at undesirable times, for example at an edge of a label in the analytical tapes according to EP 1992284 A1 (see also US 2010/0292609 A1) or at a folding edge, for example in the analytical tape described in WO 2008/043565 A2.

SUMMARY

It is therefore an object of the present invention to provide an analytical tape, a method for the production thereof and an analytical testing device which avoid the disadvantages of the prior art. In particular, it is intended to provide a production method which leads to analytical tapes of uniform thickness with the exception of the elevation caused by the lancets, so that it is also possible for an indexing mechanism to identify lancets and position them with certainty and reliability.

This object is achieved by a method, an analytical tape and an analytical testing device. Methods include those wherein the analytical tape is designed for being used in an analytical testing device with at least a sample-taking function, wherein at least one supporting tape is provided in a continuous process, and wherein a plurality of lancet elements are successively applied directly to the supporting tape at at least one application point. Advantageous developments of the invention, which can be realized individually or in any desired combination, are described further herein.

A method for producing an analytical tape is proposed. The analytical tape may be, in particular, a lancet tape, that is to say an analytical tape which comprises a plurality of analytical aids in the form of lancet elements. Alternatively, however, other types of analytical aids may also be provided in addition to the lancet elements, for example test pads which have at least one test chemical for detecting at least one analyte in a body fluid, for example for an optical and/or electrochemical detection of the analyte.

Within the scope of the present invention, a lancet element is understood here as meaning in principle any desired element by means of which a prick and/or an incision can be made in a user's skin for the purpose of producing a specimen of body fluid, for example blood or intestinal fluid. A lancet element may accordingly comprise, for example, a round or sharp tip and/or a cutting edge. A lancet element may, for example, be configured entirely or partially in the form of a round needle. Particularly preferred, however, as set out in further detail below, is the use of flat lancets, that is to say lancets which have two opposite wide sides and in which a lateral extent perpendicular to the pricking direction considerably exceeds a thickness of the lancets, for example by a factor of 10 or more. Such flat lancets may be produced, for example, from a metal tape, for example by an etching process and/or a punching process and/or a cutting process. In addition to the cutting edge or the tip, the lancet element may optionally comprise further elements, for example at least one element for collecting and/or transporting a specimen, for example a capillary and/or a capillary gap, and/or at least one testing element for detecting at least one analyte in a body fluid, for example a test chemical. In this way it is possible, for example to realize so-called microsamplers, which combine a sample-taking process with a sample-analyzing process.

The analytical tape is designed for being used in an analytical testing device with at least a sample-taking function. An analytical testing device is understood here as meaning a device which can be used in the course of a qualitative and/or quantitative detection of at least one analyte in a body fluid. The actual detection of the analyte may in this case be carried out directly by the analytical testing device itself, or the analytical testing device may merely act as an auxiliary device for the actual detecting device, for example purely as a pricking aid. Integrated testing devices with a pricking function and a detecting function are also possible. The analytical testing device has in this case at least a sample-taking function. A sample-taking function should be understood here as meaning a function by means of which a sample of the body fluid can be produced, in particular a lancet function. In addition, the analytical testing device may have further functions, for example an analyzing function for detecting the at least one analyte in the body fluid. Alternatively, however, this analyzing function may also be used by a separate analytical device. The analytical testing device may, in particular, be configured as a handheld device.

An analytical tape is accordingly understood as meaning an at least approximately continuously configured element in tape form, which comprises in one direction of the tape, that is to say along the longitudinal extent of the analytical tape, a plurality of analytical aids, for example at least 5, preferably at least 10 or even at least 20, in particular also at least 100 or at least 200, analytical aids. These analytical aids comprise lancet elements. For example, the analytical tape may exclusively comprise lancet elements as analytical aids, that is to say be configured as a lancet tape. Optionally, however, as described above, other types of analytical aids may also be provided, for example test pads. In addition, the analytical tape may, for example, comprise markings, transporting elements (such as for example eyelets or the like) or other elements.

In the method, at least one supporting tape is provided in a continuous process. A continuous process should be understood as meaning a process in which, by contrast with batch-to-batch processes, production proceeds successively and without interruption of the supporting tape. In particular, this continuous process may be a roller-to-roller process and/or the continuous process may comprise at least one such roller-to-roller process. For example, the supporting tape may be provided from a starting roller and be wound up onto a product roller after the lancet elements have been applied.

In the method, a plurality of lancet elements are successively applied directly to the supporting tape at at least one application point. In this case, it is also possible for a number of application points to be provided. For example, each application point may include a lancet applying station, for example with a punching station, in which the lancet elements are, for example, removed, for example punched out, directly from a lancet tape and/or a preliminary product. In the punching station, punching out of the lancets may take place, and preferably also at the same time positioning of the lancets. For example, a pre-etched metal tape from which the lancets are punched out may be provided. The metal tape may also comprise positioning markings, such as for example holes, which can be used for the positioning of the metal tape and/or the lancets in relation to the supporting tape and/or in relation to an apparatus. However, a different configuration of the application point is also possible in principle, for example provision of already individually separated lancets. Individually separated lancets may be transferred to the supporting tape, for example, by means of suckers, grippers, vacuum rollers or similar application elements. In this case it is possible for a single lancet element to be transferred to the supporting tape or else a number of lancet elements to be transferred to the supporting tape simultaneously, the latter for example with lancet elements already aligned in relation to one another.

Successive application should be understood here as meaning application in which the lancet elements are applied at different points of the supporting tape in a running direction of the supporting tape, for example equidistantly in the running direction. However, a non-equidistant spacing is also possible in principle. Furthermore, it is also possible in principle for a number of lancet elements to be applied in parallel at the same point of the lancet tape.

As a difference from the prior art described above, in which the lancet elements are applied to the supporting tape by means of a labeling technology, in the method according to the invention a direct application of the lancet elements to the supporting tape is therefore proposed. This means that between the lancet elements and the supporting tape there are no discontinuous intermediate elements, such as for example supporting labels, which protrude laterally, that is to say in a plane of the supporting tape, or at least in a longitudinal direction of extent of the supporting tape, over the extent of the lancet elements. There is also no use of additional connecting elements by means of which the lancet elements are flexibly connected to the supporting tape, as for example in WO 2008/043565 A2. The lancet elements therefore lie directly on the supporting tape. However, this does not rule out the possibility of the supporting tape being provided with a continuous adhesive layer, which ensures the adhesion of the lancet elements on the supporting tape. It is generally preferred within the scope of the present invention if an adhesive or an adhesive layer which is, for example, of a biocompatible configuration is used. Alternatively or in addition, the lancet elements may also be provided with a corresponding adhesive layer on their side facing the supporting tape, the adhesive layer however preferably not extending laterally beyond the lateral extent of the lancet elements. The adhesive layer therefore has in this case at most the same base area as the lancet elements or a smaller base area.

It is particularly preferred in this case if the analytical tape is configured in such a way that it has a substantially constant thickness. A substantially constant thickness is understood here as meaning within the scope of the present invention a constant thickness where, however, deviations of up to 20%, preferably of no more than 10% and particularly preferably of no more than 5%, are still tolerated. This constant thickness is in this case preferably increased only at the lancet elements by the thickness of the lancet elements. Accordingly, the analytical tape may, for example, be of a two-stage configuration, with a first thickness, that is the constant thickness of the analytical tape itself, and a second thickness in the region of the lancet elements. Changes in thickness at further elements, such as for example label edges, as known from the prior art, do not occur in this configuration.

The direct application of the lancets to the supporting tape has many advantages over the known labeling method. For instance, the analytical tape may be configured in such a way that it only includes as a change in thickness the edges of the lancet elements. At the same time, however, in the case of this method, as in the case of other methods, a high degree of sterility of the analytical tapes is ensured. The method can be configured on an industrial scale as a roller-to-roller process, so that industrial implementation of the method with high throughput rates can also be ensured.

A major advantage of the direct application of the lancet elements to the supporting tape lies in particular in the principle for identifying the transported lancet elements through the analytical testing device, for example a transporting means of the analytical testing device. For example, this transporting means may comprise a gripper and/or a sensor, for example a sensor combined with a gripper, for identifying a lancet element and for correspondingly positioning the lancet element. In this respect, reference may be made, for example, to the already previously cited WO 2008/138443 A1 (see also US 2010/0145376 A1), which can also be used within the scope of this invention. Reference can also be made to WO 2009/037341 A1 (see also US 2010/0216246 A1) and the analytical testing device described there. Particularly in such analytical testing devices, the proposed analytical tapes or analytical tapes produced by the proposed method show themselves in a particularly favorable light. For example, the lancet elements can be identified there in a simple and reliable way by the gripper. The identification by the gripper in this case preferably takes place at least partially by way of the change in thickness of the lancet element in comparison with the analytical tape outside the testing elements. By contrast with known analytical tapes and production methods using labels, in the case of which the gripper detects every change in thickness as a new lancet even though it may merely be a folding edge or a label of a different size that is concerned, in the case of the proposed analytical tapes an identification takes place with reliability and certainty. The proposed analytical tapes also meet the most demanding requirements in terms of precision, which can also be ensured at high throughput, for example with a roller-to-roller process.

The proposed method and corresponding configurations of the analytical tape can be advantageously developed in various ways. For instance, as described above, it is particularly preferred if the lancet elements comprise flat lancets, or are even configured entirely as flat lancets. In this way it is possible in particular to ensure the abrupt change in thickness described above, which is particularly advantageous for the identification of the lancet elements, in particular automatic identification. These flat lancets may be applied with one flat side to the supporting tape.

The method may preferably be carried out in such a way that at least one biocompatible adhesive and/or at least one biocompatible adhesive layer is used. This biocompatible adhesive or this biocompatible adhesive layer may, for example, be an adhesive or an adhesive layer which comes into contact with the lancet elements, in particular a cutting edge and/or a tip of the lancet elements. This biocompatible adhesive and/or this biocompatible adhesive layer may be used, for example, in order to connect the lancet elements to the supporting tape and/or in order to apply a continuous covering to the lancets. Alternatively or in addition, such a biocompatible adhesive and/or a biocompatible adhesive layer may also be used at other points.

In a further advantageous configuration of the method according to the invention, at least one continuous covering may be additionally applied to the lancets. By contrast with individual pockets or individual protective elements for the lancet elements, as are known from the prior art, such a continuous covering is therefore preferably used in the proposed method. Such a continuous covering may be applied in particular by a roller-to-roller process. When the lancet elements are used, this continuous covering may, for example, be punctured, pierced or cut through by the lancet elements. Alternatively, as described in more detail below, such a continuous covering may also be part of the supporting tape itself. In principle, however, as an alternative or in addition to a continuous covering, a discontinuous covering would also be conceivable, for example by means of individual covering patches which are individually applied. However, because of the aforementioned disadvantages, this is less preferred.

Application to the lancet elements is understood here as meaning application to a side of the lancet elements that is opposite from the supporting tape. Such a covering ensures in particular that the lancet elements are kept sterile.

Various methods may be used for producing such a continuous covering, and they can be used individually or else in combination. For example, as described above, the supporting tape itself may be used for producing the continuous covering, and to do so may be folded over along a folding edge parallel to a longitudinal direction of the supporting tape. For example, at least one edge of the supporting tape may be folded over the lancet elements after the lancet elements have been applied. For this purpose, the lancet elements may, for example, be applied to the supporting tape asymmetrically, so that a sufficient edge is available for the subsequent covering. The folded-over edge may, for example, be connected to the non-folded-over supporting tape with a material bond, in particular adhesively bonded and/or welded. The advantage of a folding method is that a folding edge is generally of a particularly impermeable configuration. For example, the lancet elements may be arranged on the supporting tape in such a way that cutting edges and/or tips of the lancet elements face the folding edge and are particularly protected by it, for example against ingress of moisture and/or contaminants. Alternatively or in addition to the production of the continuous covering by means of a folding method, it is also possible for at least one additional continuous covering tape to be applied over the lancets for producing the covering. This additional covering tape may in turn, for example, also be connected to the supporting tape with a material bond, in particular adhesively bonded and/or welded. For example, the covering tape may have a thickness of 2 to 10 micrometers, for example of 4 micrometers to 8 micrometers and particularly preferably of 6 micrometers.

The supporting tape may, for example, comprise a plastic tape. For example, it may be made of a polyethylene terephthalate (PET material) and/or a polyethylene material. The use of other types of plastics and/or other materials, for example paper materials and/or ceramic materials, is also possible in principle. Alternatively, laminate tapes, that is to say supporting tapes which are made up of a number of materials and/or a number of layers, may also be used.

The optional covering tape may also be configured correspondingly. For example, it may also be produced from a plastics material and/or another of the materials mentioned for the supporting tape. However, a configuration in which the covering tape comprises a different choice of material than the supporting tape is also possible in principle.

As described above, the lancet elements may be fixed directly on the supporting element, in particular by a connection with a material bond, preferably adhesive bonding. This adhesive bonding may be configured in various ways, for example in the form of a continuous adhesive layer on the supporting tape and/or an adhesive layer on a side of the lancet elements that is facing the supporting tape and preferably does not protrude laterally beyond the extent of the lancet elements. Accordingly, the supporting tape may, for example, comprise at least one base layer and at least one adhesive layer. The base layer may, for example, be made up of one or more of the aforementioned materials. The additional adhesive layer may, for example, be applied to this base layer as a thin layer. The application of the adhesive layer may also be part of the described method or it may already be provided as a supporting tape that has this adhesive layer. The base layer may, for example, have a thickness of 2 to 20 micrometers, in particular of 5 to 15 micrometers and particularly preferably of 6 to 12 micrometers, for example 6 micrometers or 12 micrometers. The adhesive layer may, for example, have a thickness of 5 to 30 micrometers, in particular of 10 to 20 micrometers. The adhesive layer may then be used not only for the fixing of the lancet elements but also for the fixing of the continuous covering once it has been applied. If an additional continuous covering tape is applied over the lancets, this continuous covering tape may, however, alternatively or additionally also have at least one adhesive layer.

Furthermore, the method may be configured in such a way that at least one stabilizing tape, preferably a continuous stabilizing tape, is additionally applied on a side of the supporting tape that is facing away from the lancet elements. This application of the stabilizing tape may preferably take place after the application of the lancet elements. The stabilizing tape may, for example, in turn comprise one or more of the materials described above with respect to the supporting tape. A different choice of material is also possible in principle with respect to the stabilizing tape. The stabilizing tape may, for example, have a thickness between 2 and 10 micrometers, in particular of 6 micrometers. The use of an additional stabilizing tape should in many cases be avoided in principle, since it requires at least one additional method step and can in principle be avoided if a sufficiently stable supporting tape is used. However, if the method described above is used, a method in which, for producing the continuous covering, at least one edge of the supporting tape is folded over the lancet elements after the lancet elements have been applied, the use of a thin supporting tape may be appropriate. Particularly in these cases, but also in other cases, the use of a stabilizing tape on the opposite side may then be advantageous.

As variously described above, apart from the proposed method, an analytical tape is also proposed. It may be possible in particular for this tape to be produced by a method according to the invention, as provided by one or more of the variants of an embodiment described above. Accordingly, reference can be made to the above description of the method for possible configurations of the analytical tape. The analytical tape is designed for being used in an analytical testing device with at least a sample-taking function. The analytical tape has at least one continuously formed supporting tape, a plurality of lancet elements being successively applied directly to the supporting tape. With respect to the advantages of the analytical tape, reference can be made to the above description of the method.

With reference to FIG. 5, also proposed is an analytical testing device 154, which comprises at least a sample-taking function as provided by the above description. The analytical testing device 154 may, in particular, be configured as a handheld device. The analytical testing device 154 comprises an analytical tape 112 according to the above description, that is to say in one or more of the configurations described above. Furthermore, the analytical testing device 154 has at least one transporting means 156, which is designed for bringing a lancet element 122 respectively into a position for use. For example, this position for use may be a position in which a sample-taking movement, for example a pricking movement, optionally accompanied by a collecting process for taking up body fluid, can be carried out by means of the respective lance element 122. For this purpose, the analytical testing device 154 may, for example, comprise a corresponding actuating mechanism in order to carry out the pricking movement. The transporting means 156 may, in particular, comprise a roller transporting means, for example with a good roll 158 and a bad roll 160, unused regions of the analytical tape 112 being wound up on the good roll 158 and regions with already used lancet elements 122 being wound up on the bad roll 160. Accordingly, the analytical testing device 154 may, for example, be designed for each lancet element 122 to be used only once. The transporting means 156 may, in particular, comprise at least one gripper 162, which can respectively grip at least one lancet element 122. The transporting means 156 is generally designed for identifying the presence of a lancet element 122 on the basis of a change in thickness of the analytical tape 112. On account of the use of the analytical tape 112 according to the invention, or an analytical tape 112 produced according to the invention, the advantages described above can be realized, and the transporting mechanism can perform its function in a particularly trouble-free and reliable manner. Apart from the analytical tape, reference can be made to the previously cited prior art, in particular to WO 2008/138443 A1 (see also US 2010/0145376 A1), for an exemplary configuration of the analytical testing device. However, the analytical testing device described there may also be modified, in order in particular to detect the described change in thickness, for example by means of a separate detector or sensor and/or by means of the gripper referred to. Other configurations of the analytical testing device are, however, also possible in principle.

Also proposed is an apparatus for producing an analytical tape. The apparatus is designed for carrying out a method for producing an analytical tape in one or more of the method variants described above. Accordingly, reference can largely be made to the description above, and the apparatus may respectively comprise one or more sub-apparatuses for carrying out the method steps described. For example, the apparatus may comprise at least one providing apparatus, in order to provide the at least one supporting tape in a continuous process. For example, this providing apparatus may comprise one or more rollers. Furthermore, the apparatus may comprise at least one application apparatus, for example a lancet applying station, in order to successively apply the plurality of lancet elements directly to the supporting tape at at least one application point. Further sub-apparatuses may also be provided for carrying out the optional method steps, for example at least one folding unit and/or at least one providing apparatus for at least one continuous covering, in particular a covering tape, and/or at least one providing apparatus for at least one rear covering, in particular a stabilizing tape. Exemplary embodiments of such an apparatus can be taken from the following description.

DRAWINGS

Further details and features of the invention emerge from the following description of preferred exemplary embodiments, in particular in conjunction with the subclaims. Here, the respective features may be realized by themselves alone or together in combination with one another. The invention is not restricted to the exemplary embodiments. The exemplary embodiments are schematically represented in the figures. The same designations in the individual figures refer to elements that are the same, functionally the same or correspond to one another with regard to their functions.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom.

Figure 1:
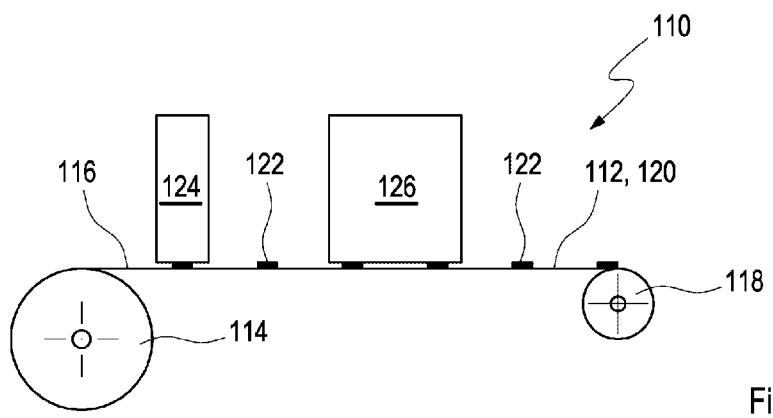
FIGS. 1A to 1D show various views of a first exemplary embodiment of a method according to the invention with a continuous covering in the form of a folding of an edge of the supporting tape.
Figure 1:
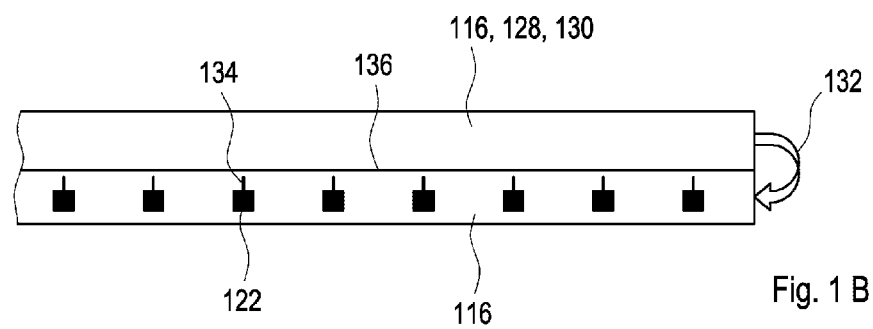
Figure 1:
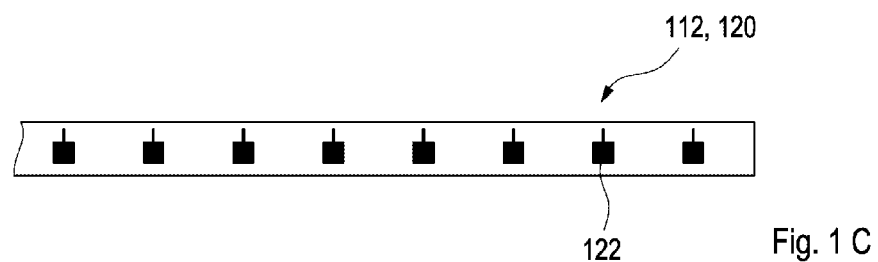
Figure 1:
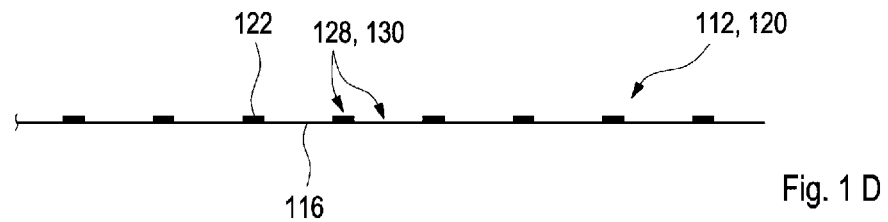

In FIGS. 1A to 1D, a first exemplary embodiment of a method according to the invention is shown in various views. FIG. 1A shows a side view of an apparatus for carrying out the method, FIG. 1B shows an intermediate product before folding over of an edge of a supporting tape and FIGS. 1C and 1D respectively show a plan view and a side view of a finished analytical tape.

In FIG. 1A, therefore, an apparatus 110 for producing an analytical tape 112 is schematically represented and will be used as a basis for explaining the first exemplary embodiment of the method. The apparatus comprises a first roller 114 for providing a supporting tape 116. After producing the analytical tape 112, the finished analytical tape 112 and/or a preliminary product of the same that can be subjected to still further method steps is wound up onto a second roller 118.

In this exemplary embodiment, the supporting tape may be, for example, a film of plastic with a thickness of 6 micrometers, onto which an adhesive layer of, for example, 10 to 20 micrometers has been applied or is applied. Accordingly, a conventional adhesive tape may be used, for example, as the supporting tape 116. For the optional adhesive layer, not separately referred to in the figures, a biocompatible adhesive is preferably used. In this way, the adhesive layer can safely come into contact with the lancet elements 122, in particular lancet tips 134 of these lancet elements 122, which later during use briefly penetrate into the body.

In this exemplary embodiment, the analytical tape 112 is configured as a lancet tape 120. Accordingly, a multiplicity of lancet elements 122 are successively applied directly to the supporting tape 116 at a lancet applying station at an application point.

Figure 4:
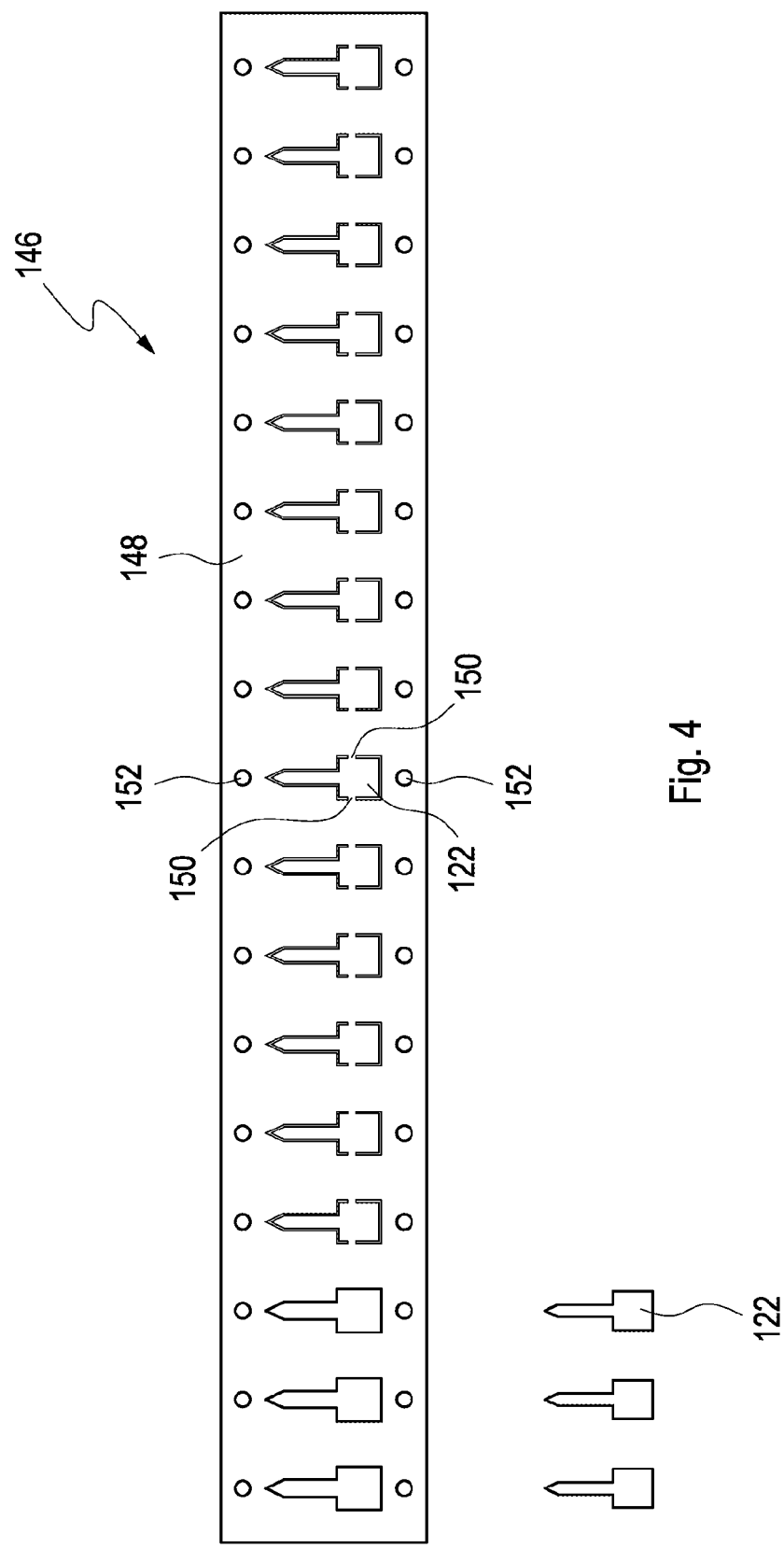
FIG. 4 shows an exemplary embodiment of a metal tape for providing a plurality of lancet elements.
Figure 5:
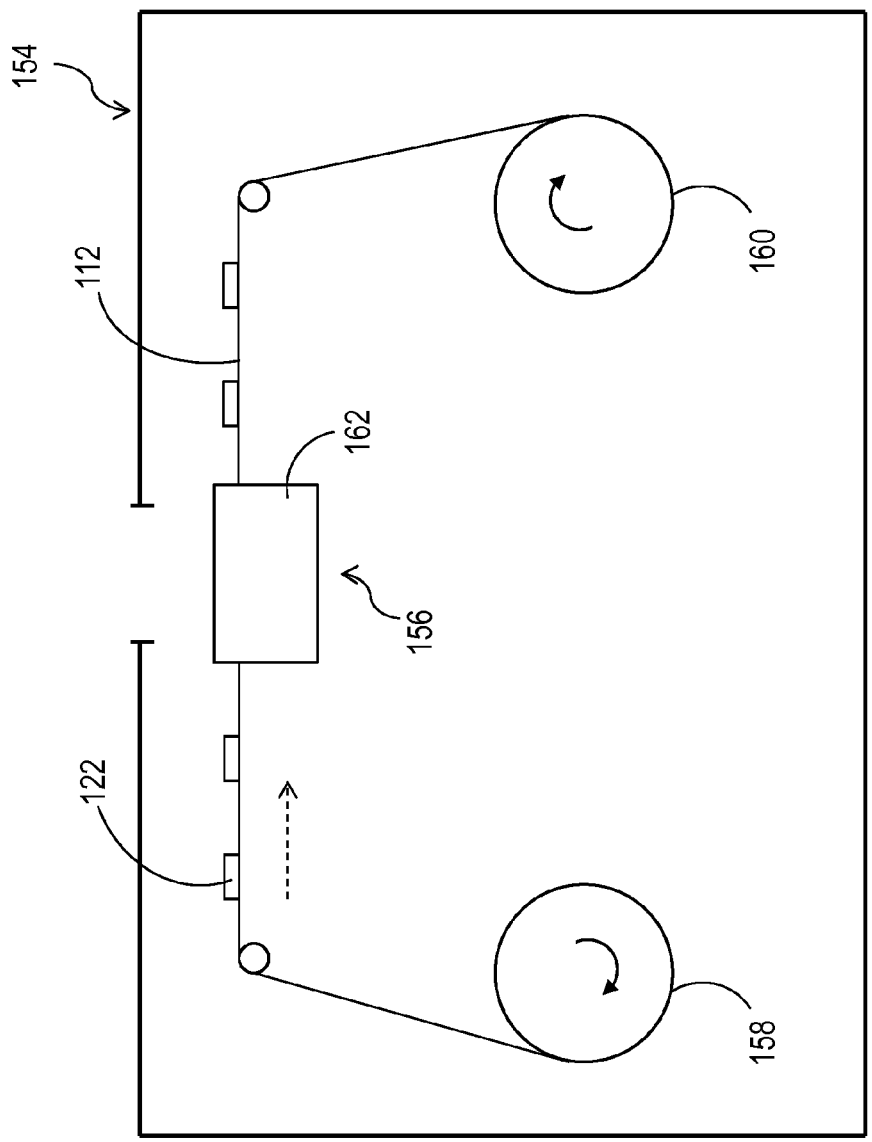
FIG. 5 shows an exemplary embodiment of an analytical testing device.

In FIG. 4, an exemplary embodiment of a metal tape 146 is represented and can be used for providing a plurality of lancet elements 122 at the lancet applying station 124, for example in a continuous roller-to-roller process. The metal tape 146 may comprise a metal supporting tape 148, from which the lancet elements 122 are pre-etched in their contours, so that, for example, they are only connected to the remaining metal supporting tape 148 by thin webs 150. These webs 150 may, for example, be severed at the lancet applying station 124, for example by a punching process and/or a cutting process. For this purpose, the lancet applying station 124 may comprise corresponding punching and/or cutting elements and/or other elements for severing the webs 150. Three already detached lancet elements 122 are shown in the lower left-hand part of FIG. 4.

Furthermore, the metal tape 146, in particular the metal supporting tape 148, may comprise one or more positioning aids, which make it possible, for example, for the metal tape 146 to be positioned in relation to the lancet applying station 124 and/or in relation to the supporting tape 116 and/or in relation to some other part of an apparatus for producing an analytical tape 112, for example the apparatus shown in FIG. 1A. In the exemplary embodiment represented in FIG. 4, holes 152 are provided as examples of such positioning aids. These holes may be provided, for example, on both sides of the lancet elements 122 in the metal supporting tape 148, so that, for example, each lancet element 122 is assigned precisely one hole 152 or precisely two such holes 152. The holes may, for example, in turn be produced by an etching process, for example by the same etching process by means of which the lancet elements 122 are also etched out from the metal supporting tape 148.

The apparatus 110 for producing the analytical tape 112 in FIG. 1A or else in other exemplary embodiments may comprise an apparatus for providing the metal tape 146, for example in turn an apparatus with one or more rollers, for example a good roll and/or a bad roll. With this apparatus, the lancet elements 122 can be provided at the lancet applying station 124. However, it is pointed out that they may also be provided in a different way, for example provided by means of a different configuration of a tape and/or provision of individual lancet elements 122, for example as piece goods and/or as individually packaged lancet elements 122. However, provision as shown in FIG. 4 can be technically realized in a particularly simple manner, and a high degree of sterility can be ensured.

As revealed by FIGS. 1B to 1C, in this configuration of the method a supporting tape 116 which is wider than the end width of the finished analytical tape 112, for example a supporting tape 116 which is at least approximately twice as wide as the end width of the finished analytical tape 112, is preferably used in the apparatus 110 as shown in FIG. 1A. As described above, this supporting tape 116 is preferably provided on the side facing the lancet applying station 124 with an adhesive layer. After the lancet elements 122 have been applied, the supporting tape 116 runs through a folding unit 126. As can be seen in FIGS. 1B and 1C, an edge 128 is thereby used as a continuous covering 130 and is folded over the lancet elements 122. The folding process is symbolically indicated in FIG. 1B by the designation 132. On account of the adhesive layer, the folded-over edge 128 adheres on the non-folded-over region of the supporting tape 116 and on the lancet elements 122, so that the latter are closed, and consequently sealed. Preferably, lancet tips 134 in this case point toward a folding edge 136, since this folding edge 136 is particularly impermeable and entails virtually no risk with respect to ensuring sterile protection. However, a different alignment is also possible in principle. In other cases, however, a minimum impermeability of the continuous covering 130 produced in this way must generally be demonstrated, since adhesively bonded edges can generally contain pores, which generally no longer ensure sterile protection. After running through the folding unit 126, the analytical tape 112 produced in this way is then wound up onto the second roller 118.

One advantage of the analytical tape 112 produced in this way and by means of the other exemplary embodiments is that it has a constant, consistently equal thickness, which is only interrupted by the lancet elements 122. Additional variations in thickness, for example in the form of steps, at labels or similar elements, generally do not occur. In this way, an indexing mechanism can be used with particular reliability and certainty in an analytical device, such as for example the testing device described in WO 2008/138443 A1 (see also US 2010/0145376 A1).

Figure 2:
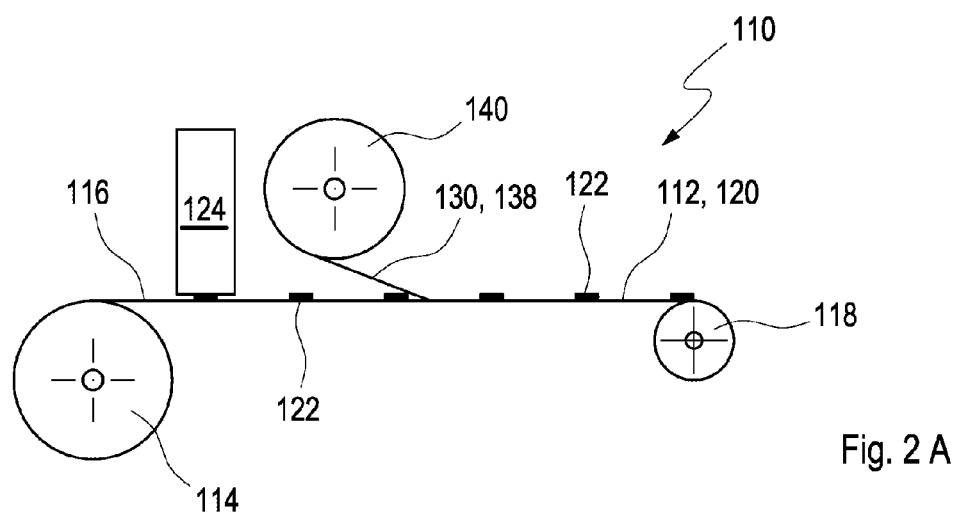
FIGS. 2A to 2C show various views of a second exemplary embodiment of a method according to the invention in which a continuous covering tape is additionally applied to produce a continuous covering.
Figure 2:
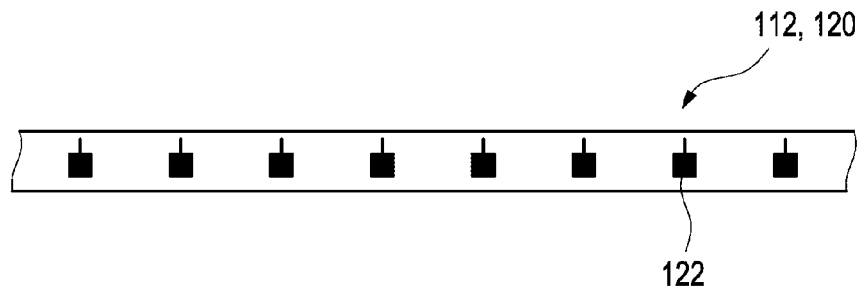
Figure 2:
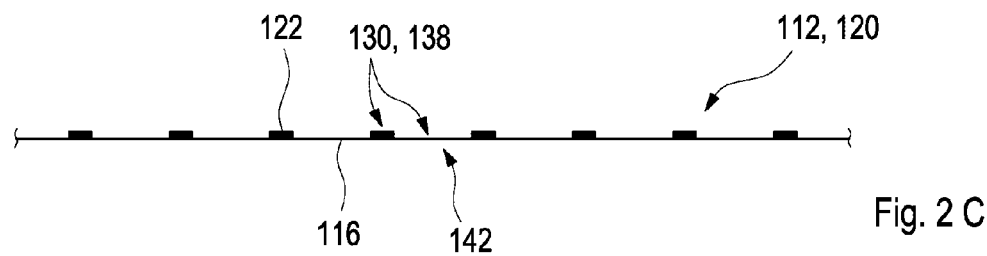

In FIGS. 2A to 2C, a second exemplary embodiment of a method according to the invention for producing an analytical tape 112 is represented, in turn in the form of a lancet tape 120. FIG. 2A shows in turn, in a representation analogous to FIG. 1A, an apparatus 110 for carrying out the method in a greatly schematized view. FIGS. 2B and 2C in turn show, in a representation analogous to FIGS. 1C and 1D, a finished analytical tape 112 respectively in plan view and in side view.

The apparatus 110 in turn comprises a first roller 114 for continuously providing a supporting tape 116, for example in turn a supporting tape 116 with an adhesive layer. The apparatus 110, which in turn may be configured for carrying out a roller-to-roller process, also comprises a second roller 118 for winding up the finished analytical tape 112 and/or an intermediate product of the same, which may subsequently be processed further. Also provided in turn is a lancet applying station 124 for applying lancet elements 122, which may, for example, in turn be configured as a punching station, as also in FIGS. 1A to 1D, and/or may comprise such a punching station.

In the case of the exemplary embodiment in FIGS. 2A to 2C, a continuous covering 130 is in turn applied over the lancet elements 122. As a difference from the folding process described in FIGS. 1A to 1D, here, however, the continuous covering is applied in the form of an additional continuous covering tape 138. This additional continuous covering tape may, for example, in turn be provided by means of a continuous process, for example a roller-to-roller process, from a third roller 140.

The supporting tape 116 may, for example, in turn comprise a film of plastic. The supporting tape may, for example, have a thickness of 12 micrometers and optionally be provided with an adhesive layer, for example an adhesive layer with a thickness of 10 to 20 micrometers, the adhesive layer preferably in turn having been applied or being applied continuously to the supporting tape 116. The covering tape 138 may, for example, be configured in the form of a covering film, for example in turn a film of plastic. The covering tape 138 may, for example, have a thickness of 6 micrometers. This serves for providing sterile protection. The covering tape 138 does not necessarily have to be provided with an adhesive layer, but may optionally additionally comprise such an adhesive layer. Preferably, in turn all the adhesive layers used in the exemplary embodiment represented are of a biocompatible configuration.

As represented in FIG. 2A, the application of the additional continuous covering tape 138 follows downstream from the application of the lancet elements 122. Furthermore, as also in the previous exemplary embodiment, additional method steps that are not represented in the figures may be provided. The finished or semifinished analytical tape 112 is then wound up onto the second roller 118.

Figure 3:
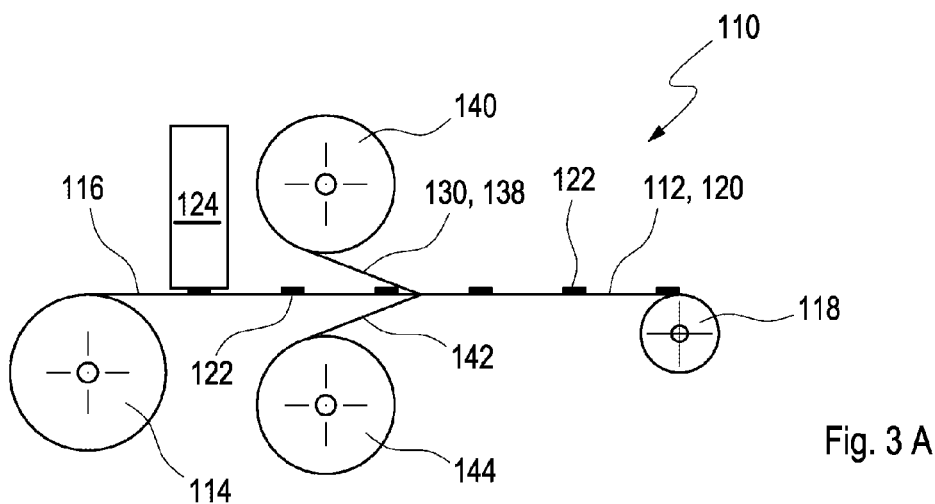
FIGS. 3A to 3C show various views of a third exemplary embodiment of a method according to the invention in which a rear stabilizing tape is additionally applied.
Figure 3:
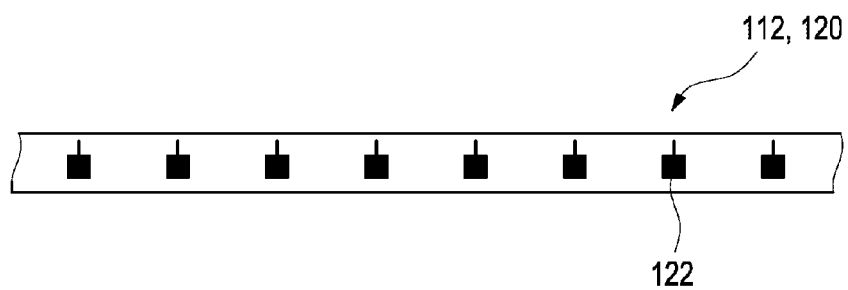
Figure 3:
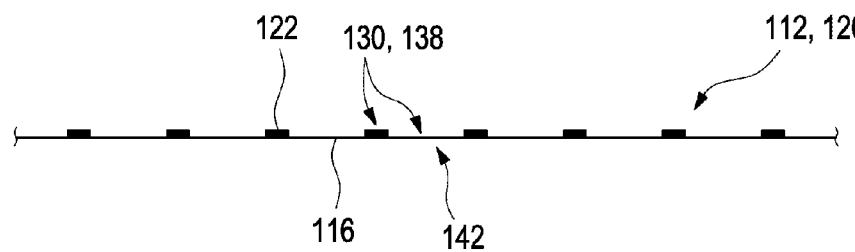

In FIGS. 3A to 3C, a third exemplary embodiment of a method according to the invention is shown in a representation analogous to FIGS. 2A to 2C. FIG. 2A shows in turn an apparatus 110 for carrying out the method, whereas FIGS. 3B and 3C show finished or semifinished products of the method in the form of an analytical tape 112, which is preferably in turn configured as a lancet tape 120.

In principle, the method proceeds initially by analogy with the method in FIGS. 2A to 2C, so that reference can largely be made to the description above. In turn, a continuous covering 130 in the form of a separate continuous covering tape 138 is applied with the applied lancet elements 122 to the supporting tape 116 with the aid of a third roller 140. In addition, however, at least one stabilizing tape 142 is applied to the supporting tape 116, for example after the lancet elements 122 have been applied, on the side of the supporting tape 116 that is facing away from the lancet elements 122. This may take place, for example, in turn by means of a continuous process, so that a continuous supporting tape 142 can be provided in a roller-to-roller process, for example from a fourth roller 144. The application of the stabilizing tape 142 may in this case take place in principle at any desired point, for example, as represented in FIG. 3A, at the same time as the application of the covering tape 138. However, a different configuration is also possible, for example earlier or later application.

In the case of this variant of the method in FIGS. 3A to 3C, for example, a thinner supporting tape 116 than in exemplary embodiments 2A and 2C can be used. For example, a supporting tape with a thickness of 6 micrometers and optionally an adhesive layer of, for example, 10 to 20 micrometers may be used. This adhesive layer may preferably be applied on both sides of the supporting tape 116. Alternatively or in addition, however, the stabilizing tape 142 may also comprise a corresponding adhesive layer, in order to fix the stabilizing tape 142 on the rear side of the supporting tape 116. The covering tape may, for example, in turn have a thickness of 6 micrometers, so that sterile protection is ensured. The stabilizing tape may, for example, have a thickness of 6 micrometers.

After production of such an analytical tape 112, the product or semifinished product produced in this way may in turn, as represented in FIG. 3A, be wound up on the second roller 118. If required, this can then be subjected to further method steps. In FIGS. 3B and 3C, finished products of the method are represented, but they can, if required, likewise be subjected to further method steps.

The exemplary embodiments represented show examples in which regular lancet tapes 120 are produced. Alternatively, however, further analytical elements may additionally be applied, for example test pads or the like.

LIST OF DESIGNATIONS 110 apparatus for producing an analytical tape
112 analytical tape
114 first roller
116 supporting tape
118 second roller
120 lancet tape
122 lancet elements
124 lancet applying station
126 folding unit
128 edge
130 continuous covering
132 folding
134 lancet tips
136 folding edge
138 covering tape
140 third roller
142 stabilizing tape
144 fourth roller
146 metal tape
148 metal supporting tape
150 webs
152 holes
154 analytical testing device
156 transporting means
158 good roll
160 bad roll
162 gripper

What is claimed is:

1. A method for producing an analytical tape designed for being used in an analytical testing device with a sample-taking function, the method comprising:
providing a supporting tape wound on a first roller;
unwinding the supporting tape from the first roller in a transport direction and subsequently winding the supporting tape onto a second roller in a continuous process;
punching lancets from a lancet tape at a punching station; and
successively applying the lancets directly to the supporting tape at at least one application point between the first and second rollers, wherein each of the plurality of lancets comprises a puncturing component selected from the group consisting of a flat lancet and a round needle, each of the puncturing components being fixed directly on the supporting tape and being oriented pointing in a direction perpendicular to the transport direction, and wherein the combination of the supporting tape and the lancets forms the analytical tape configured having a constant thickness, the constant thickness being increased only at the lancets by the thickness of the lancets.

2. The method as claimed in claim 1, wherein the lancets comprise flat lancets, the flat lancets being applied with one flat side to the supporting tape.

3. The method as claimed in claim 1, wherein at least one biocompatible adhesive and/or at least one biocompatible adhesive layer are used.

4. The method as claimed in claim 1, wherein the supporting tape has at least one base layer and at least one adhesive layer.

5. The method as claimed in claim 4, wherein the base layer has a thickness of 2 to 20 micrometers.

6. The method as claimed in claim 5, wherein the base layer has a thickness of 6 to 12 micrometers.

7. The method as claimed in claim 4, wherein the adhesive layer has a thickness of 5 to 30 micrometers.

8. The method as claimed in claim 7, wherein the adhesive layer has a thickness of 10 to 20 micrometers.

9. The method as claimed in claim 1, wherein at least one continuous covering is additionally applied to the lancets.

10. The method as claimed in claim 9, wherein, for producing the continuous covering, at least one edge of the supporting tape is folded over the lancets after the lancets have been applied.

11. The method as claimed in claim 10, wherein the folded-over edge is connected to the non-folded-over supporting tape with a material bond.

12. The method as claimed in claim 11, wherein the folded-over edge is adhesively bonded and/or welded to the non-folded-over supporting tape.

13. The method as claimed in claim 9, wherein, for producing the continuous covering, at least one additional continuous covering tape is applied over the lancets.

14. The method as claimed in claim 13, wherein the covering tape has a thickness of 2 to 10 micrometers.

15. The method as claimed in claim 14, wherein the covering tape has a thickness of 4 to 8 micrometers.

16. The method as claimed in claim 1, wherein at least one stabilizing tape is additionally applied on a side of the supporting tape that is facing away from the lancets.

17. The method as claimed in claim 16, wherein the stabilizing tape has a thickness between 2 and 10 micrometers.

18. An analytical tape that can be produced as claimed in claim 1.

19. An analytical testing device, having at least a sample-taking function, comprising the analytical tape as claimed in claim 18, wherein the analytical testing device has at least one transporting means, the transporting means being designed for bringing one of the lancets respectively into a position for use, wherein the transporting means is designed for identifying the presence of one of the lancets on the basis of a change in thickness of the analytical tape.

20. An analytical device as claimed in claim 19, wherein the transporting means comprises a gripper.

21. An apparatus for producing an analytical tape, wherein the apparatus is designed for carrying out the method as claimed in claim 1, wherein the apparatus comprises at least one application apparatus, in order to successively apply the plurality of lancets directly to the supporting tape at at least one application point.

22. The method of claim 1, further comprising folding a portion of the supporting tape in a lateral direction perpendicular to the transport direction such that the lancets are at least partially covered by the portion of the supporting tape to protect the lancets from contamination, wherein the portion of the supporting tape is folded in the lateral direction after the lancets are applied to the supporting tape and before the supporting tape is wound onto the second roller.

23. The method of claim 1, further comprising aligning the lancet tape relative to the supporting tape using a plurality of positioning aides, wherein each of the positioning aides corresponds to one of the lancets of the lancet tape.

24. The method of claim 23, wherein the lancets are oriented on the lancet tape such that the lancets extend longitudinally in a direction perpendicular to a longitudinal direction of the lancet tape.

25. The method of claim 24, wherein the lancet tape includes a plurality of pairs of the positioning aides, each of the pairs of positioning aides is aligned with a corresponding one of the lancets.

26. The method of claim 23, wherein the positioning aides include a plurality of holes.

27. The method of claim 26, wherein each lancet is assigned one or more of the holes.

28. The method of claim 26, wherein each lancet is assigned precisely one or precisely two of the holes.

29. The method of claim 26, wherein the holes are provided on both sides of the lancets.

30. A method for producing an analytical tape designed for being used in an analytical testing device with a sample-taking function, the method comprising:

providing a supporting tape wound on a first roller;

unwinding the supporting tape from the first roller in a transport direction and subsequently winding the supporting tape onto a second roller in a continuous process;

aligning a lancet tape relative to the supporting tape using a plurality of positioning aides, the positioning aides being positioned in a predetermined spatial relationship to one or more of a plurality of lancets of the lancet tape;

punching the lancets from the lancet tape at a punching station; and successively applying the lancets directly to the supporting tape at at least one application point between the first and second rollers, wherein each of the plurality of lancets comprises a puncturing component selected from the group consisting of a flat lancet and a round needle, each of the puncturing components being fixed directly on the supporting tape and being oriented pointing in a direction perpendicular to the transport direction, and wherein the combination of the supporting tape and the lancets forms the analytical tape configured having a constant thickness, the constant thickness being increased only at the lancets by the thickness of the lancets.

31. The method of claim 30, wherein the lancets are oriented on the lancet tape such that the lancets extend longitudinally in a direction perpendicular to a longitudinal direction of the lancet tape.

32. The method as claimed in claim 31, wherein at least one stabilizing tape is additionally applied on a side of the supporting tape that is facing away from the lancets.

33. The method of claim 32, further comprising folding a portion of the supporting tape in a lateral direction perpendicular to the transport direction such that the lancets are at least partially covered by the portion of the supporting tape to protect the lancets from contamination, wherein the portion of the supporting tape is folded in the lateral direction after the lancets are applied to the supporting tape and before the supporting tape is wound onto the second roller.

34. The method of claim 30, wherein the lancet tape includes a plurality of pairs of the positioning aides, each of the pairs of positioning aides is aligned with a corresponding one of the lancets.

35. The method of claim 30, wherein the positioning aides include a plurality of holes.

36. The method of claim 35, wherein each lancet is assigned one or more of the holes.

37. The method of claim 36, wherein each lancet is assigned precisely one or precisely two of the holes.

38. The method of claim 35, wherein the holes are provided on both sides of the lancets.

* * * * *